United States Patent [19]

Valentine et al.

[11] Patent Number: 5,292,534

[45] Date of Patent: Mar. 8, 1994

[54] SUSTAINED RELEASE COMPOSITION AND METHOD UTILIZING XANTHAN GUM AND AN ACTIVE INGREDIENT

[75] Inventors: William Valentine; William K. Valentine, both of Lawrenceville, Ga.

[73] Assignee: Valentine Enterprises, Inc., Lawrenceville, Ga.

[21] Appl. No.: 857,516

[22] Filed: Mar. 25, 1992

[51] Int. Cl.$^5$ .............................................. A61K 9/48
[52] U.S. Cl. ................................... 424/451; 424/457; 424/469; 424/489; 424/470
[58] Field of Search ............... 424/451, 457, 469, 470, 424/489

[56] References Cited

U.S. PATENT DOCUMENTS

| | | | |
|---|---|---|---|
| 4,203,997 | 5/1980 | Kuppers et al. | 424/280 |
| 4,454,125 | 6/1984 | Demopoulos | 424/201 |
| 4,539,143 | 9/1985 | Boden et al. | 424/70 |
| 4,777,033 | 10/1988 | Ikura et al. | 424/44 |
| 4,911,917 | 3/1990 | Kuhrts | 424/10 |
| 4,965,252 | 10/1990 | Kuhrts | 514/54 |
| 5,002,774 | 3/1991 | Agrawala | 424/469 |
| 5,023,245 | 6/1991 | Kuhrts | 514/54 |
| 5,051,261 | 9/1991 | McGinity | 424/451 |
| 5,096,714 | 3/1992 | Kuhrts | 424/457 |
| 5,120,762 | 6/1992 | Hanaoka et al. | 514/474 |

*Primary Examiner*—Thurman K. Page
*Assistant Examiner*—William E. Benston
*Attorney, Agent, or Firm*—DeLio & Peterson

[57] ABSTRACT

A compacted sustained release composition for delivering a drug as an active ingredient to the gastro-intestinal tract comprises an effective amount of the active ingredient in mixture with xanthan gum, the active ingredient comprising in excess of 40 percent by weight of the total of the active ingredient and the xanthan gum, the mixture being in the form of a unit dose in capsule or tablet form. In addition to niacin, the active ingredient may be an analgesic, antipyretic, anti-inflammatory agent, vitamin, electrolyte replenisher, decongestant, antihistamine, and useful bacteriological organisms for the gastro-intestinal tract.

71 Claims, No Drawings

SUSTAINED RELEASE COMPOSITION AND METHOD UTILIZING XANTHAN GUM AND AN ACTIVE INGREDIENT

BACKGROUND OF THE INVENTION

This invention relates to a composition and method of manufacture and use in which xanthan gum is combined with an active pharmaceutical or other ingredient in a compacted dose form for delivering the active ingredient to the gastro-intestinal tract over a sustained period.

Sustained or slow release compositions containing pharmaceutical medications or other active ingredients are designed to contain higher concentrations of the medicament or ingredient and are prepared in such a manner as to effect sustained or slow release into the gastro-intestinal digestive tract of humans or animals over an extended period of time. Well absorbed oral sustained or slow release therapeutic drug dosage forms have inherent advantages over conventional, immediate release dosage forms. The advantages include less frequent dosing of a medicament and resultant patient regime compliance, a more sustained drug blood level response, the possibility of effecting therapeutic action with less ingested drug, and the mitigation of side effects. By providing a slow and steady release of the medicament over time, absorbed drug concentration spikes are mitigated or eliminated by effecting a smoother and more sustained blood level response.

Many therapeutic agents, medicaments, or other active ingredients have a wide window for absorption, meaning that the drug has been demonstrated to be well absorbed along the entire digest tract. Such agents, medicaments, or other active ingredients are then logical candidates for possible dosage as a sustained or slow release medication.

Sustained or slow release therapeutic dose forms are based on many and varied principles. For example, one of the techniques of preparation involves formation of the drug in generally spherical pellet form wherein a specific quantity of pellets are set aside for immediate release and the remaining drug pellets or spheres are coated with various thicknesses of a suitable fat, or resinous, or fatty resinous like coating. When fractions of the pellets are blended together and then filled into capsules or pressed into tablets, without destroying the integrity of the coatings, suitable slow or sustained release dose forms may be effected. Another technique is to admix the therapeutic agent with fats and solid polyhydric alcohols, such as polyoxyethylene glycol, and/or a solid surfactant, such as polyoxyethylene glycol distearate, and press the mixture into tablets to form an erosion matrix to effect slow or sustained release dosage forms. Another method employs the use of a therapeutic agent bound to an ion exchange resin or otherwise complexed with an organic or inorganic molecule and imbedded in a waxy core or granule and administered in capsule or pressed tablet form. Still another method employs the use of an indigestible film former such as methylcellulose applied to a powder or granule base containing a therapeutic agent followed by subsequent forming into compressed tablets to effect slow or sustained release. Yet another method employs a tablet containing a specific drug coated with an indigestible film in which the film is pierced by a laser beam to allow for a small and precise portal from which the drug is slowly released.

As a result of the increased awareness of the importance of hypercholesterolemia and its relationship to coronary heat disease during the last several years, there has been an increased emphasis on treatment with niacin (nicotinic acid). Guidelines for adults have recently been published by the National Cholesterol Education Program, coordinated by the National Heart, Lung and Blood Institute, which state that a desirable blood cholesterol level is below 5.17 mmol/liter. Approximately half of adults screened have been found to have a total blood cholesterol level above the desired range, and accordingly, are encouraged to see a physician for further analysis and instruction. It has been recommended that clinicians use a bile acid sequesterant or niacin as first line therapy for treatment of hypercholesterolemic patients. Niacin is also the oldest of the pharmacologic agents used in the treatment of hyperlipidemia and, since its introduction in 1955, it has been in continuous use either monadically, or in combination with bile acid binding resin therapy.

In doses of 3–6 g/day, which exceed its requirements as a B Vitamin, niacin (but not niacinamide) is highly effective in reducing elevated levels of plasma cholesterol and triglycerides. Niacin inhibits adipose tissue lipolysis, reduces plasma free fatty acid levels and decreases very low density lipoprotein synthesis, thereby decreasing the production of low density lipoproteins from the very low density lipoproteins. Niacin is of demonstrated value in preventing manifestations of arteriosclerotic heart disease, having been shown to decrease recurrent nonfatal myocardial infarction in the coronary drug project by 40% without concurrent increase in mortality from nonarteriosclerotic causes as has been observed with clofibrate.

Niacin is readily absorbed from the stomach and intestinal tract and has no difficulty passing the tissue barrier. Following per os administration of a tablet or capsule dosage of niacin peak plasma levels are obtained within 15-30 minutes in humans. The drug is rapidly distributed in the various tissues including kidney and adipose tissue with a slower metabolism of liver and brown fat. Also of note is the observation that niacin has the ability to penetrate the blood brain barrier.

Niacin is rapidly eliminated from plasma and its elimination halflife in humans is 20–45 minutes. Although large doses of 3–6 g/day of niacin are required to decrease circulating cholesterol and triglycerides in humans, it does not appear that the high peak serum levels attained are required, since the lipid lowering effect is maintained after plasma niacin levels are below the limit of sensitivity of the analytical method used. Thus, there is no correlation between systemic levels of niacin and its pharmacological effect.

The chief drawback to using niacin in the treatment of hyperlipidemia is facial and truncal flushing, which occurs in nearly all users shortly after ingestion of tablets with as small a dosage as 75 mg of niacin per tablet. It appears that niacin induces flushing by increasing the formation and/or release of some prostaglandin, which in turn increases the production of cyclic amp. However, this mechanism does not appear to mediate the effect of niacin on lipolysis. The side effects of truncal flushing, nausea, gastro-intestinal upset, and rectal itching experienced following the ingestion of high potency niacin tablets (500 mg/tablet) has contributed to patient dropout of niacin therapy introduced to treat hyperlipidemia.

It has been difficult to produce a slow or sustained release niacin product by the conventional methods of barrier coating or erosion-type mechanisms. The classic concept of a sustained release dosage regimen is to release 20-35% of the therapeutic agent within the first hour and to sustain the remaining portion of the therapeutic agent over a 8-12 hour period. When one considers that the niacin therapeutic dose is 500-1000 mg and that niacin will cause a flushing response in most subjects with a dosage release of more than 75 mg within a one hour period, the problem becomes apparent. Nicobid, marketed by Armour Pharmaceuticals, has been the most widely marketed sustained release dose form of niacin in recent years. Clinical evaluations of the Nicobid dose form of 500 mg niacin per tablet indicate that the side effects have still not been ameliorated, and the main side effect of flushing is still responsible for a patient dropout rate approaching 20%. Therefore, some new method of slow release is required to cope with the specific problem presented by the niacin dose form requirements.

Bearing in mind the problems and deficiencies of the prior art, it is therefore an object of the present invention to provide a composition and method of manufacture and use which delivers an active pharmaceutical or other ingredients in a dose form to the gastro-intestinal tract of humans and animals over a sustained period.

It is another object of the present invention to provide a composition which delivers niacin, in large dose forms well above 75mg, to the gastro-intestinal tract without the side effects of flushing and itching.

It is a further object of the present invention to provide a sustained release composition and method of manufacture and use which is useful with a wide number of active pharmaceutical and other ingredients.

It is yet another object of the present invention to provide a composition which delivers active pharmaceutical and other ingredients in which the active ingredients may be present in relatively large quantities compared to the remaining components of the composition.

SUMMARY OF THE INVENTION

The above and other objects, which will be apparent to those skilled in the art, are provided in the present invention which relates to a simplified method of effecting a clinically validatable slow or sustained release of active pharmaceutical or other ingredients by combining the active ingredient with xanthan gum, compacting the combinate and size reducing the compact to form powders or capsules, or by combining the active ingredient with xanthan gum and a suitable lubricant and forming tablets by direct tablet compression techniques.

In one aspect, the invention comprises a compacted sustained release composition for delivering a drug such as niacin as an active ingredient to the gastro-intestinal tract comprising an effective amount of the active ingredient in mixture with xanthan gum, the active ingredient comprising in excess of 40 percent by weight of the total of the active ingredient and the xanthan gum, the mixture being in the form of a unit dose in capsule or tablet form. The method corresponding to this aspect comprises producing a compacted sustained release composition for delivering a drug such as niacin as an active ingredient to the gastro-intestinal tract by mixing an effective amount of the active ingredient with xanthan gum, the active ingredient comprising in excess of 40 percent by weight of the total of the active ingredient and the xanthan gum, and forming the mixture in a unit dose in capsule or tablet form.

In another aspect, the invention comprises a compacted sustained release composition for delivering a drug as an active ingredient to the gastro-intestinal tract comprising an effective amount of the active ingredient in mixture with xanthan gum, the active ingredient being selected from the group consisting of analgesics, antipyretics, anti-inflammatory agents, vitamins, electrolyte replenishers, decongestants, antihistamines, and useful bacteriological organisms for the gastro-intestinal tract, the mixture being in the form of a unit dose in capsule or tablet form. The method corresponding to this aspect comprises producing a compacted sustained release composition for delivering a drug as an active ingredient to the gastro-intestinal tract by mixing an effective amount of the active ingredient with xanthan gum, and forming the mixture in a unit dose in capsule or tablet form.

The active ingredient(s) may be agglomerated with a water soluble carbohydrate based agglomerate prior to mixing with the xanthan gum. Preferably, the mixture of active ingredient(s) and xanthan gum is directly compressed into unit dose tablets. Alternatively, the mixture of active ingredient(s) and xanthan gum is compacted and reduced in size to fill unit dose capsules.

DETAILED DESCRIPTION OF THE PREFERRED EMBODIMENTS

The sustained release mechanism of the present invention is based on the concept of phoresis wherein the release rate of niacin or other active pharmaceutical or other ingredient is controlled by producing a tablet which forms a gel following ingestion. In order for the niacin or other active ingredient to be released to the gastro-intestinal tract in a slow and sustained manner, it is necessary for the ingredient to pass uniformly and slowly through the gel. The release of the active component through the gel mass is slow and steady and is controlled by the amount of the gel former used to effect the system.

In accordance with the present invention, xanthan gum has been found to be the most effective gel former used to produce the slow release of niacin or other active ingredient in dose form. Xanthan gum is a high molecular weight natural carbohydrate, or, more specifically, a polysaccharide. Xanthan gum defines the exocellular biopolysaccharide which is produced in a pure culture fermentation process by the microorganism "Xanthomonas Campestris". In the fermentation, "Xanthomonas Campestris" is cultured in a well aerated medium containing commercial glucose, a suitable nitrogen source, dipotassium hydrogen phosphate, and appropriate trace elements.

The polysaccharide coating formed surrounding the cell wall, xanthan gum, must be stable and hydrophilic in order to protect the organism from dehydration during periods of adverse conditions. The polymer structure, molecular weight, and gel forming characteristics of the cell wall coating are constant and reproducible under given conditions of fermentation. At the conclusion of the fermentation process, xanthan gum is recovered by precipitation in isopropyl alcohol, then dried and milled. The molecular weight of the xanthan gum polymer is probably in the order of 2 million but has been reported to be as high as 13-50 million. These reported differences are most probably due to association phenomena between the polymer chains. The xanthan gum is preferably obtained for processing in the present invention in dry, free flowing granular or powder form, with a preferred particle size range of about 20-200 U.S. Mesh (850-74 microns).

In accordance with the present invention, a clinically validatable slow or sustained release of active pharmaceutical or other ingredients is prepared by combining the active ingredient(s) with xanthan gum, compacting the combinate and size reducing the compact to form powders or capsules, or, in a more preferred embodiment, by combining the active ingredient(s) with xanthan gum and a suitable lubricant and forming tablets by direct tablet compression techniques.

The active pharmaceutical or other ingredients which may be utilized in combination with xanthan gum include, in addition to niacin (nicotinic acid or 3-pyridinecarboxylic acid), any other pharmaceutical or drug having a beneficial effect on the body when released to the gastro-intestinal tract in a slow or sustained manner. Preferably, the active ingredient or agent is also provided in dry, free flowing granular or powder form, with a preferred particle size range of about 20-200 U.S. Mesh (850-74 microns). Such ingredients may be, for example, analgesic, antipyretic, and/or anti-inflammatory agents such as aspirin, acetaminophen and ibuprofen, vitamins such as pyridoxine (vitamin B-6) hydrochloride and cyanocobalamin (vitamin B-12), calcium ascorbate, electrolyte replenishers such as potassium chloride, decongestants such as pseudoephedrine hydrochloride, antihistamines such as chlorpheniramine maleate, or useful bacteriological organisms for the gastro-intestinal tract such as lactobacillus acidophyllus.

The active ingredient or agent may be combined directly with the xanthan gum, as will be described below, or may be preliminarily combined with a low density, highly porous, generally spherical, water soluble carbohydrate-based agglomerates of maltodextrin, dextrose, sucrose, fructose or other agglomerated corn syrup solid, for example. Any of the water soluble carbohydrate-based agglomerate may be co-agglomerated with each other prior to or during combination with the active ingredient.

The preferred agglomerate is maltodextrin, a low conversion starch hydrolyzate having a D.E. (dextrose equivalent) less than 20, an example being VELite 1000 maltodextrin available from Valentine Enterprises, Inc. of Lawrenceville Ga. comprised of Maltrin M-100 maltodextrin available from Grain Processing Corp.

When the active ingredient is to be preliminarily combined with the water soluble carbohydrate-based agglomerate, the components are preferably agglomerated in a fluid bed agglomerator by standard spray granulation techniques. The active ingredient is combined with water soluble carbohydrate-based agglomerate and produced as dry, free flowing granules of a desired particle size, for example, about 20-100 U.S. mesh (850-149 microns). The important characteristic is that the active ingredient is contained in or on the carbohydrate-based agglomerate and is immediately available, and is stable in the formulation with the xanthan gum. No coatings such as wax or other compositions are placed over the active ingredient which would interfere with dissolution of the active ingredient. It has been discovered that xanthan gum alone may be employed in the final product to effect slow and sustained release in the body.

After the active ingredient is provided in its desired form, either as essentially pure granules or in the agglomerated form described above, it is admixed with the desired amount of xanthan gum, preferably by low shear mixing such as that encountered in a planetary, ribbon or plow mixer. The relative amounts of active ingredient and xanthan gum may be varied as desired. It has been unexpectedly discovered that a considerably higher amount of active ingredient, particularly niacin, may be employed relative to the xanthan gum while still retaining the desired effect of slow and sustained release in the gastro-intestinal tract of humans or animals. In particular, the mixture may employ in excess of 40% by weight of active ingredient, and even a major amount of active ingredient, in the final dose form, whether it be in compacted and reduced to powder for filling in capsules or directly compressed into tablet form. In the case of niacin as the active ingredient, this is a considerably higher relative amount than can be employed when another gum, such as guar gum, is employed, where limits of 33% by weight of niacin have been reported. In the present invention, the amount of active ingredient may more preferably range from 50-80% by weight of the total mixture, and the amount of xanthan gum is preferably not less than 20% by weight, more preferably from 20-50% by weight of the total composition.

After the mixing process, the mixture of active ingredient and xanthan gum is compacted and size reduced, and then made into desired unit dose form such as filled capsules Compaction may be by standard techniques such as slugging where tablets are pressed or by roller compaction. In either case, the compacted tablets or rolls of the mixture are ground to reduce the particle size of the mixture, e.g., to a particle size of about 20-100 U.S. mesh (850-149 microns), and then filled into the final capsule dose form. Preferably, to achieve best sustained release characteristics, the mixture may be directly compressed by standard techniques into final tablet dose form. A lubricant such as stearic acid may be added in an amount of 0.1-5% by weight of the total composition to assist in the tableting process.

By following the process of the present invention to produce tablets in the form described, 1000 mg doses of niacin have been able to be formulated in tablets containing xanthan gum in the ranges specified and ingested by humans without a flushing response Since as little as 75 mg/hr. of niacin has been shown to produce flushing, this indicates that the present invention is able to deliver the niacin in slow and/or sustained quantities over as much as 24 hours or more.

It is theorized that an important function of xanthan gum in the present invention is control of aqueous fluid rheology It has been found that concentrated aqueous solutions of xanthan gum exhibit extreme pseudoplasticity The xanthan gum/active ingredient tablet dose forms a gel sol (a hydrated gel) when exposed to the environment in the stomach It is believed that when intestinal shear stress is applied to the solvated tablet dose form the viscosity of the xanthan gum gel is reduced and concomitantly spread to allow the drug niacin to phorese or pass through the gel mass.

Once the xanthan gum/active ingredient tablet enters the digestive tract it is subjected to the shear forces of the digestive action and movement which are believed to be sufficient enough to reach the yield point of the xanthan gel sol. The yield point of the xanthan gum sol can be considered to be the quantity of force required to dissociate some of the "super junction zones" of the xanthan gum and the shear thinning that results allows for the spread of the gel sol.

A principal advantage of xanthan over other gums such as guar gum is its greater purity and lot to lot uniformity of composition. Its resistance to bacterial breakdown means also that xanthan feeding adds little short-chain faulty acids via bacterial decomposition of the gum in the small or large intestine. It is also believed to be safe as in reported studies, quantities of 12 g/day of xanthan gum were ingested each day for a period of 12 weeks with no severe adverse digestive symptoms. In another study, following a 7-day control period, 5 male volunteers consumed, on each of 23 consecutive days, a weight of xanthan gum equal to 15 times the current acceptable daily intake of 10 mg/kg body weight, as approved by the EEC and by the joint FAO/WHO Expert Committee on Food Additives. Measurements before and at the end of the test period showed that the ingestion of xanthan, as a prehydrated gel, acted as a bulking agent in terms of its effects on fecal wet and dry weight and intestinal transit times but had no significant effect on plasma biochemistry Haematological indices, urinalysis parameters, glucose tolerance and insulin tests, serum immunoglobulins, triglycerides, phospholipids and high density lipoproteins, breath hydrogen and breath methane concentrations. There was, however, a moderate (10%) reduction in serum cholesterol and a significant increase in fecal bile acid concentrations. The data indicate that the ingestion of xanthan caused no adverse dietary nor physiological effects in any of the test subjects. In particular, all of the enzymatic and other parameters that act as sensitive indicators or adverse toxicological effects remained unchanged.

Positive effects of xanthan ingestion are believed to be its lack of toxicity and also its ability to bind or otherwise increase bile acid content in the feces. It is obvious that any increase in bile acid in the stool will have a positive effect when dealing with hyperlipidemia. Even though the test quantities were of a high level, it is apparent that the effect of bile acid elimination and the non formation of free fatty acids is a desirable effect even when the quantities of xanthan are relatively limited.

One additional clinical observation on the use of xanthan gum in obesity can shed some additional light on the use of smaller quantities of xanthan gum to modify serum lipidology. Body weight and cholesterol and triglycerides in blood were estimated in 2 groups of 10 women, 20 to 50 years of age, with body mass index of 30–40 before and 30–60 days following ingestion of 2 550 mg capsules of xanthan gum with 250 ml of water 3 times per day or starch placebo capsules with 250 ml of water 3 times per day. In each case the capsules were administered before meals. After 30 and 60 days of treatment with xanthan gum body weight decreased by 2.9 and 7.7 kg, cholesterol by 18.8 and 20.5 and triglycerides by 12.9 and 15.5 mg/100 ml, respectively. Differences were significant compared with the placebo group. There was also a significant sensation of satiety at 90 min, and at 5 hours after each meal with those subjects on the xanthan gum regimen. Even at this level (3 gm xanthan gum/day), significant serum lipid changes were apparent.

EXAMPLES

The following illustrative examples are given to more particularly illustrate the specific details of the practice of the present invention. Equivalent procedures and quantities will occur to those skilled in the art and, therefore, the following examples are not meant to define the limits of the present invention, these being defined by the appended claims. All references to percentages in the examples, as throughout the specification, are to weight percentage, unless otherwise identified.

EXAMPLE 1

Examples of successful niacin/xanthan gum tablet formulations and their method of preparation are as follows:

| Formulation No. VL5-079 | |
| --- | --- |
| Niacin Base Granulation: | |
| Niacin (Nicotinic Acid) Roche | 97.0% |
| Maltodextrin M-100 | 3.0% |

The niacin was charged into a fluid bed agglomerator and the maltodextrin was sprayed over as a 15% aqueous solution to effect agglomeration and compressibility with concomitant good flow characteristics. The final granulation was sized −20 mesh, U.S. sieve size.

| Formulation No. VL5-080C | |
| --- | --- |
| Niacin Base Granulation (No. VL5-079) | 61.9% |
| Xanthan Gum (Keltrol SF) | 37.4% |
| Stearic Acid | 0.7% |

The components were well mixed and compressed on caplet punches at a weight of 840 mg/tablet at a hardness of 12 kp.

| | | |
| --- | --- | --- |
| Each 840 mg Tablet yields: | Niacin | 504.4 mg |
| | Xanthan Gum | 314.2 mg |
| | Stearic Acid | 5.9 mg |
| | Maltodextrin | 15.5 mg |
| 1 × 840 mg Tablet 3x/day yields: | Niacin | 1500 mg |
| | Xanthan Gum | 942 mg |
| 2 × 840 mg Tablets 3x/day yields: | Niacin | 3000 mg |
| | Xanthan Gum | 1882 mg |
| 3 × 840 mg Tablets 3x/day yields: | Niacin | 4500 mg |
| | Xanthan Gum | 2824 mg |

This formulation was used in tests with subjects to evaluate flushing. No adverse effects have been noted dosing two tablets.

The quantity or percentage composition relative to the xanthan gum has been raised and lowered from the base formulation (VL5-080C). The least xanthan quantity that has, up until now, produced no flushing is noted below.

| Formulation No. VL5-117E | |
| --- | --- |
| Niacin Base Granulation (No. VL5-079) | 76.4% |
| Xanthan Gum (Keltrol SF) | 22.7% |
| Stearic Acid | 0.9% |

The materials were mixed and compressed into tablets having a weight of 680 mg at a hardness of 12 kp.

Single tablet trials resulted in no adverse flush reaction.

COMPARATIVE EXAMPLE 1

Utilizing the procedure to make the base formulation, No. VL5-080C, the xanthan gum was replaced with guar gum. After ingestion in test subjects, flushing was found to occur relatively quickly (within 2-3 hours). When half of the xanthan gum was replaced with guar gum, flushing occurred after 2 hours. Based upon the trials employed, the effect of slow release of niacin appears to be due to the presence of the xanthan gum and that mixed gum systems of xanthan and guar gum are not as effective.

Results similar to those experienced with guar gum can also be demonstrated with the use of locust bean gum. It appears that guar and locust bean gums are liable to the enzymatic digestive mode. A mixed system of niacin with approximately equal amounts of either guar gum or locust bean gum and xanthan gum results in flushing approximately 2 hours after ingestion of the slow release niacin tablets. Xanthan gum is believed to be better able to resist enzymatic digestion, liquefication, or in some other manner of destruction of the gel structure than either the guar gum or the locust bean gum.

EXAMPLE 2

| FORMULATION No. VL4-081 | |
| --- | --- |
| Niacin was agglomerated in a Freund Mini Flow Coater fluid bed agglomerator as follows: | |
| In Bed: | |
| Niacin (Lump Free in Fine Powder) | 400 gm |
| In Solution: | |
| Maltrin M-100 (GPC) | 12.5 gm |
| Water | 112.5 gm |
| Flow Control @ 55% | |
| Air for atomization 10 PSI (Coarse) | |
| Spray Rate @ 3.5 | |
| Spray @ 1 Minute | |
| Pulse Jet @ .1 & .1 | |
| Air Inlet 80C | |
| Terminal Dry @ 42 C. | |
| Total solution overall will yield 97% niacin agglomerates | |
| Pass agglomerates through 20 mesh | |

The agglomerates from No. V14-079 were then blended with xanthan gum as follows:

| Niacin Base Granulation | 61.9% |
| --- | --- |
| Xanthan Gum (Keltrol Gm) (coarse granule) | 37.4% |
| Stearic acid (fine powder) | 0.7% |

Blend the materials for 10 minutes then compress on capsule shape punches at 840 mg/tablet at maximum pressure (18-20 KP).

| Each tablet yields: | |
| --- | --- |
| Niacin | 504.4 mg |
| Xanthan Gum | 314.2 mg |
| Maltrin M-100 | 15.5 mg |
| Stearic acid | 5.9 mg |
| Total Tablet Weight | 840.0 mg |
| Tablet Weight Specification (Average weight 10 tablets) | 840.0 mg + 3% (840 mg-885 mg) |
| 2 tablets 3x/day yields: | |
| Niacin | 3,000 mg/day |
| Xanthan Gum | 1,884 mg/day |

After taking the aforementioned doses of two niacin tablets, three times per day, the test subjects showed no flushing. All of the test subjects showed satisfactory recovery of niacin and nicotinuric acid from urine.

Thus, the combinate of xanthan gum and niacin provides a therapeutic dose form that obviates the flushing reaction associated with large doses of niacin. While flush response is usually triggered by approximately 75 mg of niacin, in the combinate of the present invention, we are able to provide dose quantities of niacin of 1000 mg without a flushing response.

EXAMPLE 3

Agglomerated/granulated niacin base was prepared in a Freund Model 80 fluid bed agglomerator according to the following formulation:

| In Product Container: | |
| --- | --- |
| Niacin Powder U.S.P. | 40 kg |
| Pump Solution: | |
| 10 D.E. Maltodextrin Maltrin M-100 (Grain Processing Corp.) | 1.23 kg |
| Distilled Water | 11.07 kg |
| Atomizing gun pressure | 3.0 atm |
| Atomizing air volume | 150 m$^3$/hr |
| Pattern air volume | 20 m$^3$/hr |

The product bowl was secured and fluidization was initiated with inlet air at 80° C. Alternate spraying and shaking of the filters to return un-agglomerated fines to the bowl was continued until all of the pump solution was delivered to the fluidized bed. The product was dried, removed, and sized to −20 mesh and packaged.

A blend for tableting was prepared as follows:

| Agglomerated Niacin | 61.9% |
| --- | --- |
| Xanthan Gum (TIC) | 37.4% |
| Stearic acid (fine powder U.S.P.) | 0.7% |

8.0 kg of the prepared blend for tableting was compressed on caplet shaped punches at a weight of 840 mg/tablet, with each tablet containing 540 mg of niacin.

A crossover clinical study indicated that the formulation is effective in cholesterol lowering and was essentially flush response free.

EXAMPLE 4

Tablets were prepared as follows:

| Compression granulated Niacin (Lonza) U.S.P. | 60.0% |
| --- | --- |
| Xanthan Gum (Kelco K-7B170) | 39.3% |
| Stearic Acid N.F (fine powder) | 0.7% |

The components were mixed and blended to effect a product suitable for compression.

Tablets were compressed on capsule shaped punches and dies at a weight of 840 mg to yield tablets containing 504 mg niacin per tablet.

A 6 patient availability indicated satisfactory recovery with no flushing following a 2 tablet dose.

EXAMPLE 5

Tablets were prepared as follows:

| Niacin fine powder U.S.P. (Roche) | 50.0% |
| --- | --- |

| | |
|---|---|
| Xanthan Gum (fine powder) | 49.3% |
| Stearic Acid (fine powder U.S.P.) | 0.7% |

6.0 kg of material were blended and further granulated by compaction to yield 20-60 mesh granules. The granules were filled into two piece hard gelatin capsules at a fill weight of 450 mg and contained 225 mg niacin per capsule.

In a 6 patient evaluation, urinary tracing indicated satisfactory release of the niacin. Two capsule and four capsule dosing equivalent to 500 and 1000 mg niacin per dose indicated no flushing.

Other active ingredients were tested as follows:

EXAMPLE 6

A tableting base was mixed from the following components:

| | |
|---|---|
| Acetamenophen (coarse granular) | 65.0% |
| Xanthan Gum (granular) | 34.3% |
| Stearic Acid N.F. (fine powder) | 0.7% |

A 5 kg blend of the tableting base was prepared and pressed into tablets at a weight of 770 mg per tablet equivalent to 500 mg acetamenophen per tablet.

EXAMPLE 7

A tableting base was mixed from the following components:

| | |
|---|---|
| Aspirin (coarse crystals) | 61.9% |
| Xanthan Gum (Keltrol) | 37.4% |
| Stearic acid N.F. (fine powder) | 0.7% |

A 10 kg blend of the tableting base was prepared and pressed into tablets at a weight of 815 mg per tablet equivalent to 500 mg acetylsalicylic acid per tablet.

EXAMPLE 8

A tableting base was mixed from the following components:

| | |
|---|---|
| Ibuprofen powder | 60.0% |
| Xanthan Gum (Keltrol) | 39.3% |
| Stearic acid N.F. (fine powder) | 0.7% |

A 5 kg of the tableting base was prepared and pressed into tablets at a weight of 667 mg per tablet equivalent to 400 mg ibuprofen per tablet.

EXAMPLE 9

A tableting base was mixed from the following components:

| | |
|---|---|
| Potassium chloride USP (fine crystals) | 60.0% |
| Xanthan Gum (Ketrol) | 39.3% |
| Stearic acid N.F. (fine powder) | 0.7% |

A 5 kg blend of the tableting base was prepared and pressed into tablets at a weight of 834 mg equivalent to 500 mg of potassium chloride per tablet.

EXAMPLE 10

A tableting base was mixed from the following components:

| | |
|---|---|
| Lactobacillus Achidophylluss (4 billion organisms/gm) | 50.0% |
| Xanthan Gum powder (Keltrol) | 49.3% |
| Stearic acid N.F. (fine powder) | 0.7% |

A 1 kg blend of the tableting base was prepared and pressed into tablets at a weight of 500 mg equivalent to 250 mg of lactobacillus acidophyllus culture per gm billion organisms.)

EXAMPLE 11

A tableting base was mixed from the following components:

| | |
|---|---|
| Acetamenophen | 54.8% |
| Chlorpheniramine Maleate | 0.6% |
| Pseudoephedrine HCl | 4.6% |
| Xanthan Gum | 39.3% |
| Stearic acid N.F. (fine powder) | 0.7% |

A 1 kg blend of the tableting base was prepared and pressed into tablets at a weight of 650 mg. The tablets were equivalent to:

| | |
|---|---|
| Acetamenophen | 6356 mg |
| Chlorpheniramine Maleate | 30 mg |
| Pseudoephedrine HCl | 4 mg |

EXAMPLE 12

A tableting base was mixed from the following components:

| | |
|---|---|
| Calcium Ascorbate | 65.0% |
| Xanthan Gum | 34.3% |
| Stearic acid N.F. (fine powder) | 0.7% |

A 1 kg blend of the tableting base was prepared and pressed into tablets at a weight of 900 mg/tablet. Each tablet was equivalent to 585 mg of ascorbic acid.

EXAMPLE 13

A tableting base was mixed from the following components:

| | |
|---|---|
| Pyridoxine HCl/Maltodextrin Co-agglomerate | 65.0% |
| Xanthan Gum | 34.3% |
| Stearic acid N.F. (fine powder) | 0.7% |

A 1 kg blend of the tableting base was prepared and pressed into tablets at a weight of 650 mg/tablet. Each tablet wa s equivalent to 50 mg of pyridoxine hydrochloride.

EXAMPLE 14

A tableting base was mixed from the following components:

| | |
|---|---|
| Cyanocobalamine/Maltodextrin/ | 65.0% |

| -continued | |
|---|---|
| Dextrose Co-agglomerate Xanthan Gum | 34.3% |
| Stearic acid N.F. (fine powder) | 0.7% |

A 1 kg blend of the tableting base was prepared and pressed into tablets at a weight of 650 mg/tablet. Each tablet was equivalent to 75 meq of cyanocobalamine (vitamin B-12).

The compositions incorporating xanthan gum in the foregoing examples 6-14 exhibit satisfactory sustained release of the active ingredients therein into the gastrointestinal tract.

While this invention has been described with reference to specific embodiments, it will be recognized by those skilled in the art that variations are possible without departing from the spirit and scope of the invention, and that it is intended to cover all changes and modifications of the invention disclosed herein for the purposes of illustration which do not constitute departure from the spirit and scope of the invention.

Having thus described the invention, what is claimed is:

1. A sustained release composition for slow delivery of a drug as an active ingredient to the gastro-intestinal tract consisting of an effective amount of said active ingredient in mixture with xanthan gum and a lubricant, the mixture being in the form of a compacted unit dose, said active ingredient being present in an amount of 40-80 weight percent of said unit dose, said xanthan gum being present in an amount of 20-50 weight percent of said unit dose.

2. A method of producing a sustained release composition for slow delivery of a drug as an active ingredient to the gastro-intestinal tract consisting of mixing an effective amount of said active ingredient with xanthan gum and a lubricant, said active ingredient being present in an amount of 40-80 weight percent of said unit dose, said xanthan gum being present in an amount of 20-50 weight percent of the mixture, compacting the mixture and forming the mixture into a unit dose.

3. A sustained release composition for slow delivery of niacin as an active ingredient to the gastro-intestinal tract consisting of an effective amount of niacin in mixture with xanthan gum and a lubricant, the mixture being in the form of a compacted unit dose, said niacin being present in an amount of 40-80 weight percent of said unit dose, said xanthan gum being present in an amount of 20-50 weight percent of said unit dose.

4. A method of producing a sustained release composition for slow delivery of niacin as an active ingredient to the gastro-intestinal tract consisting of mixing an effective amount of niacin with xanthan gum and a lubricant, said niacin being present in an amount of 40-80 weight percent of said unit dose, said xanthan gum being present in an amount of 20-50 weight percent of the mixture, compacting the mixture and forming the mixture into a unit dose.

5. A sustained release composition for slow delivery of a drug as an active ingredient to the gastro-intestinal tract consisting of an effective amount of said active ingredient in mixture with xanthan gum, the mixture being in the form of a unit dose in capsule or tablet form, said active ingredient being present in an amount of 40-80 weight percent of said unit dose, said xanthan gum being present in an amount of 20-50 weight percent of said unit dose.

6. The composition of claim 5 wherein said active ingredient is niacin.

7. The composition of claim 5 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

8. The composition of claim 5 wherein said unit dose comprises a major amount by weight of said active ingredient and a minor amount by weight of xanthan gum.

9. The composition of claim 5 wherein said active ingredient is niacin and said unit dose comprises a major amount by weight of niacin and a minor amount by weight of xanthan gum.

10. The composition of claim 5 wherein said active ingredient is combined with a water soluble, carbohydrate-based agglomerate.

11. A method of producing a sustained release composition for slow delivery of a drug as an active ingredient to the gastro-intestinal tract consisting of mixing an effective amount of said active ingredient with xanthan gum, said active ingredient being present in an amount of 40-80 weight percent of said mixture, said xanthan gum being present in an amount of 20-50 weight percent of said mixture, compacting the mixture and forming the mixture into a unit dose in capsule or tablet form.

12. The method of claim 11 wherein said active ingredient is niacin.

13. The method of claim 11 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

14. The method of claim 11 wherein said mixture comprises a major amount by weight of said active ingredient and a minor amount by weight of xanthan gum.

15. The method of claim 11 wherein said mixture comprises a major amount by weight of niacin and a minor amount by weight of xanthan gum.

16. The method of claim 11 further including combining said active ingredient with a water soluble, carbohydrate-based agglomerate prior to mixing with said xanthan gum.

17. A sustained release composition for slow delivery of a drug as an active ingredient to the gastro-intestinal tract consisting of an effective amount of said active ingredient, xanthan gum and a lubricant, the mixture being in the form of a unit dose in capsule or tablet form, said active ingredient being present in an amount of 40-80 weight percent of said unit dose and said xanthan gum being present in an amount of 20-50 weight percent of said unit dose.

18. The composition of claim 17 wherein said active ingredient is niacin.

19. The composition of claim 17 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

20. The composition of claim 17 wherein said active ingredient comprises between 50 and 80 weight percent of said unit dose.

21. The composition of claim 20 wherein said active ingredient is niacin.

22. The composition of claim 20 wherein said active ingredient is selected from the group consisting of analgesics, antipyretics, anti-inflammatory agents, vitamins, electrolyte replenishers, decongestants, antihistamines, and useful bacteriological organisms or the gastro-intestinal tract.

23. A method for producing a sustained release composition for slow delivery of a drug as an active ingredient to the gastro-intestinal tract consisting of mixing an effective amount of said active ingredient, xanthan gum and a lubricant, said active ingredient being present in an amount of 40–80 weight percent of said mixture and said xanthan gum being present in an amount of 20–50 weight percent of said mixture, compacting the mixture and forming the mixture into a unit dose in capsule or tablet form.

24. The method of claim 23 wherein said active ingredient is niacin.

25. The method of claim 23 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

26. The method of claim 23 wherein said active ingredient comprises between 50 and 80 weight percent of said mixture.

27. The method of claim 26 wherein said active ingredient is niacin.

28. The method of claim 26 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

29. A sustained release composition for slow delivery of a drug as an active ingredient to the gastro-intestinal tract consisting of an effective amount of said active ingredient, a water soluble carbohydrate-based agglomerate, xanthan gum, and a lubricant, the mixture being in the form of a unit dose in capsule or tablet form, said active ingredient being present in an amount of 40–80 weight percent of said unit dose and said xanthan gum being present in an amount of 20–50 weight percent of said unit dose.

30. The composition of claim 29 wherein said active ingredient is niacin.

31. The composition of claim 29 wherein said active ingredient is selected from the group consisting of analgesics, antipyretics, anti-inflammatory agents, vitamins, electrolyte replenishers, decongestants, antihistamines, and useful bacteriological organisms for the gastro-intestinal tract.

32. The composition of claim 1 wherein said active ingredient is an analgesic.

33. The composition of claim 1 wherein said active ingredient is an antipyretic.

34. The composition of claim 1 wherein said active ingredient is an anti-inflammatory agent.

35. The composition of claim 1 wherein said active ingredient is a vitamin.

36. The composition of claim 1 wherein said active ingredient is an electrolyte replenisher.

37. The composition of claim 1 wherein said active ingredient is a decongestant.

38. The composition of claim 1 wherein said active ingredient is an antihistamine.

39. The composition of claim 1 wherein said active ingredient is a useful bacteriological organism for the gastro-intestinal tract.

40. The method of claim 2 wherein said active ingredient is an analgesic.

41. The method of claim 2 wherein said active ingredient is an antipyretic.

42. The method of claim 2 wherein said active ingredient is an anti-inflammatory agent.

43. The method of claim 2 wherein said active ingredient is a vitamin.

44. The method of claim 2 wherein said active ingredient is an electrolyte replenisher.

45. The method of claim 2 wherein said active ingredient is a decongestant.

46. The method of claim 2 wherein said active ingredient is an antihistamine.

47. The method of claim 2 wherein said active ingredient is a useful bacteriological organism for the gastro-intestinal tract.

48. The composition of claim 5 wherein said active ingredient is an analgesic.

49. The composition of claim 5 wherein said active ingredient is an antipyretic.

50. The composition of claim 5 wherein said active ingredient is an anti-inflammatory agent.

51. The composition of claim 5 wherein said active ingredient is a vitamin.

52. The composition of claim 5 wherein said active ingredient is an electrolyte replenisher.

53. The composition of claim 5 wherein said active ingredient is a decongestant.

54. The composition of claim 5 wherein said active ingredient is an antihistamine.

55. The composition of claim 5 wherein said active ingredient is a useful bacteriological organism for the gastro-intestinal tract.

56. The method of claim 4 wherein said active ingredient is an analgesic.

57. The method of claim 11 wherein said active ingredient is an antipyretic.

58. The method of claim 11 wherein said active ingredient is an anti-inflammatory agent.

59. The method of claim 11 wherein said active ingredient is a vitamin.

60. The method of claim 11 wherein said active ingredient is an electrolyte replenisher.

61. The method of claim 11 wherein said active ingredient is a decongestant.

62. The method of claim 11 wherein said active ingredient is an antihistamine.

63. The method of claim 11 wherein said active ingredient is a useful bacteriological organism for the gastro-intestinal tract.

64. The composition of claim 29 wherein said active ingredient is an analgesic.

65. The composition of claim 29 wherein said active ingredient is an antipyretic.

66. The composition of claim 29 wherein said active ingredient is an anti-inflammatory agent.

67. The composition of claim 29 wherein said active ingredient is a vitamin.

68. The composition of claim 29 wherein said active ingredient is an electrolyte replenisher.

69. The composition of claim 29 wherein said active ingredient is a decongestant.

70. The composition of claim 29 wherein said active ingredient is an antihistamine.

71. The composition of claim 29 wherein said active ingredient is a useful bacteriological organism for the gastro-intestinal tract.

* * * * *

UNITED STATES PATENT AND TRADEMARK OFFICE
CERTIFICATE OF CORRECTION

PATENT NO. : 5,292,534

DATED : March 8, 1994

INVENTOR(S) : Valentine, et al.

It is certified that error appears in the above-identified patent and that said Letters Patent is hereby corrected as shown below:

Column 12, Line 31, "6356 mg" should read - - 356 mg - -.

Signed and Sealed this

Twelfth Day of July, 1994

Attest:

BRUCE LEHMAN

Attesting Officer

Commissioner of Patents and Trademarks